(12) United States Patent
Masuda et al.

(10) Patent No.: US 12,265,069 B2
(45) Date of Patent: Apr. 1, 2025

(54) GAS CONCENTRATION MEASUREMENT SYSTEM

(71) Applicant: Asahi Kasei Microdevices Corporation, Tokyo (JP)

(72) Inventors: Masanori Masuda, Tokyo (JP); Yuta Takagi, Tokyo (JP)

(73) Assignee: Asahi Kasei Microdevices Corporation, Tokyo (JP)

( * ) Notice: Subject to any disclaimer, the term of this patent is extended or adjusted under 35 U.S.C. 154(b) by 198 days.

(21) Appl. No.: 18/186,191

(22) Filed: Mar. 20, 2023

(65) Prior Publication Data

US 2023/0349876 A1 Nov. 2, 2023

(30) Foreign Application Priority Data

Mar. 30, 2022 (JP) ................. 2022-057668
Mar. 8, 2023 (JP) ................. 2023-036062

(51) Int. Cl.
*G01N 21/3504* (2014.01)
*G01N 21/31* (2006.01)
*G01N 33/00* (2006.01)

(52) U.S. Cl.
CPC ..... *G01N 33/0062* (2013.01); *G01N 21/3504* (2013.01); *G01N 2021/3181* (2013.01); *G01N 2201/062* (2013.01); *G01N 2201/12* (2013.01)

(58) Field of Classification Search
CPC ... G01N 2021/1704; G01N 2021/3181; G01N 21/274; G01N 21/3504; G01N 2201/062; G01N 2201/12; G01N 2201/1211; G01N 33/0062

See application file for complete search history.

(56) References Cited

U.S. PATENT DOCUMENTS

| | | | |
|---|---|---|---|
| 5,886,348 A | 3/1999 | Lessure et al. | |
| 2007/0029487 A1* | 2/2007 | Wong | G01N 21/3151 250/339.13 |
| 2016/0231244 A1* | 8/2016 | Camargo | H01L 31/0304 |

FOREIGN PATENT DOCUMENTS

| | | | |
|---|---|---|---|
| JP | 2014016268 A | 1/2014 | |
| JP | 2017015508 A | 1/2017 | |
| JP | 2017015567 A | 1/2017 | |
| JP | 2018109619 A | 7/2018 | |
| JP | 2018110222 A | 7/2018 | |

* cited by examiner

*Primary Examiner* — Hina F Ayub
(74) *Attorney, Agent, or Firm* — KENJA IP LAW PC

(57) ABSTRACT

Provided are a gas concentration measurement system, gas concentration computation section, and gas concentration measurement method enabling high-accuracy gas concentration measurement. The gas concentration measurement system includes: a gas concentration measurement section (10a) including a light-emitting element (11) and a first sensor element; a light-emitting element drive section that drives the light-emitting element; a signal acquisition section (21) that acquires at least an output signal of the first sensor element, a first drive signal that is a first voltage value or first current value of the light-emitting element, and a second drive signal that is a second voltage value or second current value of the light-emitting element; and a computation section (22) that computes gas concentration based on signals acquired by the signal acquisition section. The computation section, based on the first and second drive signals, corrects the output signal of the first sensor element and computes the gas concentration.

16 Claims, 12 Drawing Sheets

GAS CONCENTRATION MEASUREMENT SYSTEM

CROSS-REFERENCE TO RELATED APPLICATIONS

The present application claims priority of Japanese Patent Application No. 2022-057668 (filed Mar. 30, 2022) and Japanese Patent Application No. 2023-036062 (filed Mar. 8, 2023), the entire contents of which are incorporated herein by reference.

TECHNICAL FIELD

The present disclosure relates to a gas concentration measurement system, a gas concentration computation section, and a gas concentration measurement method.

BACKGROUND

Non-dispersive infrared gas concentration measurement devices are conventionally known examples of gas concentration measurement devices that measure the concentration of a measurement target gas in the atmosphere. A non-dispersive infrared gas concentration measurement device measures the gas concentration of a measurement target gas through detection of the amount of absorption of infrared light by exploiting the fact that the wavelength of infrared light that is absorbed differs depending on the type of gas. Gas concentration measurement devices are also referred to as gas sensors.

There are situations in which it is necessary to correct the amount of light emission by a light-emitting element or an output signal of a light-receiving element in a gas sensor. For example, a device that is described in Patent Literature (PTL) 1 controls a light-emitting element based on temperature information and humidity information.

CITATION LIST

Patent Literature

PTL 1: JP 2018-110222 A

SUMMARY

Although the technique in PTL 1 compensates for effects caused by temperature and humidity, there is demand for a technique that enables even higher accuracy gas concentration measurement.

In view of the situation set forth above, an object of the present disclosure is to provide a gas concentration measurement system, a gas computation section, and a gas concentration concentration measurement method that enable maintenance of high-accuracy gas concentration measurement.

A gas concentration measurement system according to an embodiment of the present disclosure comprises:
 a gas concentration measurement section including a light-emitting element and a first sensor element;
 a light-emitting element drive section that drives the light-emitting element;
 a signal acquisition section that acquires at least an output signal of the first sensor element, a first drive signal that is a first voltage value or a first current value of the light-emitting element, and a second drive signal that is a second voltage value or a second current value of the light-emitting element; and
 a computation section that computes a gas concentration based on signals acquired by the signal acquisition section, wherein
 the computation section, based on the first drive signal and the second drive signal, corrects the output signal of the first sensor element and computes the gas concentration.

A gas concentration computation section according to an embodiment of the present disclosure is a gas concentration measurement section including a light-emitting element and a first sensor element and comprises:
 a light-emitting element drive section that drives the light-emitting element;
 a signal acquisition section that acquires at least an output signal of the first sensor element, a first drive signal that is a first voltage value or a first current value of the light-emitting element, and a second drive signal that is a second voltage value or a second current value of the light-emitting element; and
 a computation section that computes a gas concentration based on signals acquired by the signal acquisition section, wherein
 the computation section, based on the first drive signal and the second drive signal, corrects the output signal of the first sensor element and computes the gas concentration.

A gas concentration measurement method according to an embodiment of the present disclosure is a gas concentration measurement method performed by a gas concentration measurement system that includes:
 a gas concentration measurement section including a light-emitting element and a first sensor element;
 a light-emitting element drive section that drives the light-emitting element;
 a signal acquisition section that acquires at least an output signal of the first sensor element, a first drive signal that is a first voltage value or a first current value of the light-emitting element, and a second drive signal that is a second voltage value or a second current value of the light-emitting element; and
 a computation section that computes a gas concentration based on signals acquired by the signal acquisition section,
 the gas concentration measurement method comprising the computation section, based on the first drive signal and the second drive signal, correcting the output signal of the first sensor element and computing the gas concentration.

According to the present disclosure, it is possible to provide a gas concentration measurement system, a gas concentration computation section, and a gas concentration measurement method that enable high-accuracy gas concentration measurement.

DETAILED DESCRIPTION

Figure 1:
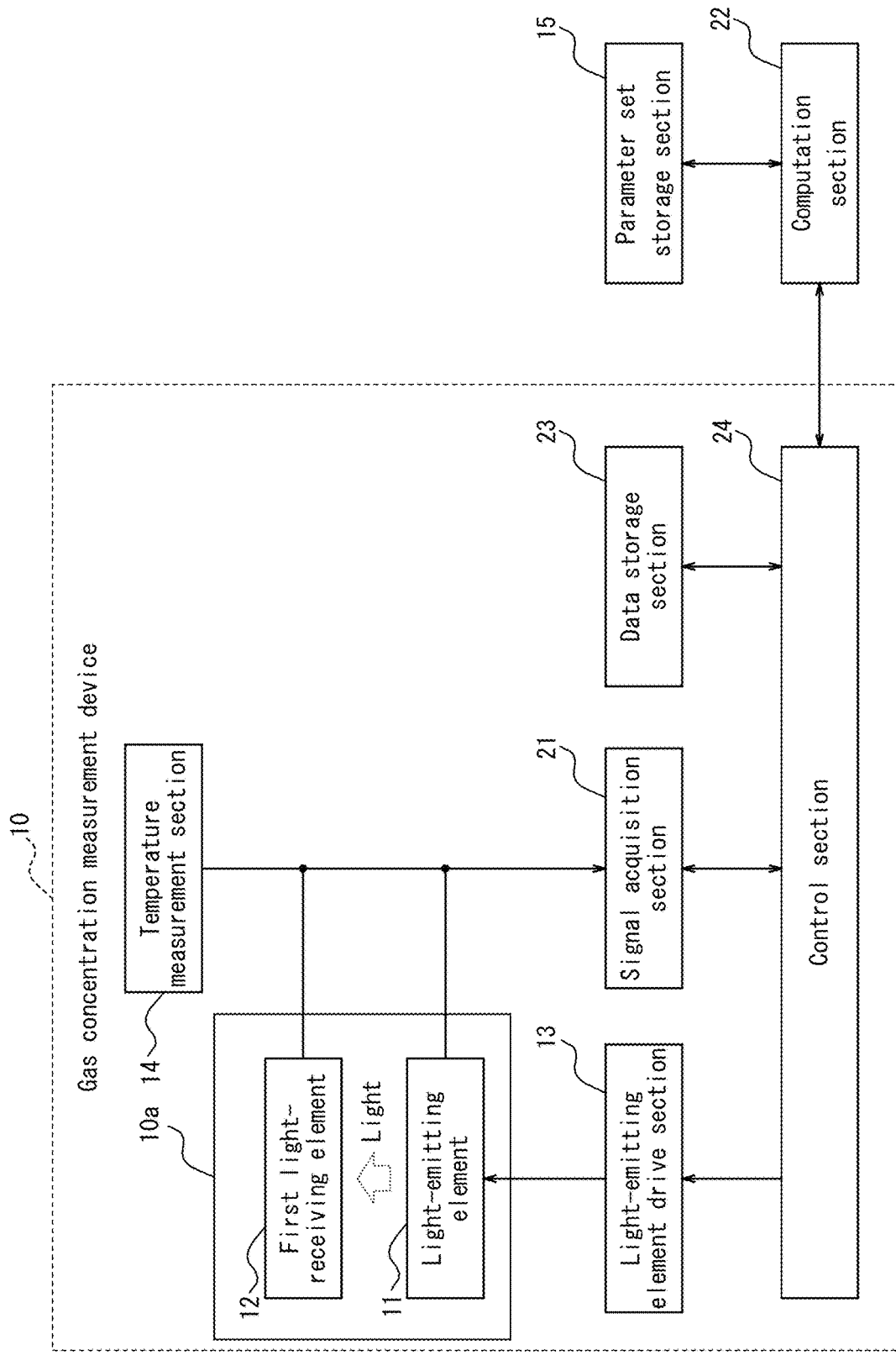
FIG. 1 is a diagram illustrating a configuration example of a gas concentration measurement system according to an embodiment of the present disclosure.

The following describes a gas concentration measurement system, a gas concentration computation section, and a gas concentration measurement method according to an embodiment of the present disclosure with reference to the drawings. Parts in the drawings that are the same or correspond are allotted the same reference signs. In description of the present embodiment, descriptions of parts that are the same or correspond may be omitted or abbreviated as appropriate.

<Gas Concentration Measurement System>

FIG. 1 is a diagram illustrating a configuration example of a gas concentration measurement system 1 according to the present embodiment. The gas concentration measurement system 1 includes a gas concentration measurement device 10 that is a measurement section of a non-dispersive infrared (NDIR) gas sensor, a parameter set storage section 15, and a computation section 22 that computes a gas concentration based on a signal detected by the gas concentration measurement device 10. The gas concentration measurement system 1 measures the gas concentration through detection of the amount of absorption of infrared light by exploiting the fact that the wavelength of infrared light that is absorbed differs depending on the type of gas. The measurement target gas may be $CO_2$, alcohol, methane, or the like, for example, but is not limited to these gases.

<Gas Concentration Measurement Device and Gas Concentration Measurement Section>

In the present embodiment, the gas concentration measurement device 10 includes a gas concentration measurement section 10a, a light-emitting element drive section 13, a temperature measurement section 14, a signal acquisition section 21, a data storage section 23, and a control section 24. The gas concentration measurement section 10a includes a light-emitting element 11 and a first light-receiving element 12 in the present embodiment.

(Light-Emitting Element)

The light-emitting element 11 outputs light including a wavelength that is absorbed by the measurement target gas. Specific examples of the light-emitting element 11 include a lamp, a light-emitting diode (LED), and a microelectromechanical systems (MEMS) light source. In the present embodiment, the light-emitting element 11 is an infrared LED.

(First Sensor Element)

A first sensor element may be a quantum optical sensor that measures an amount of light or may be a soundwave sensor (microphone) that detects pressure change due to light absorption by a gas. Detection of the amount of light absorption may be direct measurement of an amount of light or may be indirect detection through pressure changing due to light absorption by a gas. Moreover, the detection signal may be a current value or a voltage value that is output from the quantum optical sensor or soundwave sensor. Furthermore, the detection signal may be a signal that is further amplified or modified from an output current value or voltage value. In the present embodiment, the first sensor element is a light-receiving element (first light-receiving element 12). The first light-receiving element 12 has sensitivity to a band of light including a wavelength that is absorbed by the measurement target gas. As a specific example, the first light-receiving element 12 may be a quantum sensor such as a photodiode having a PIN structure. In the present embodiment, the first light-receiving element 12 is a quantum infrared sensor.

(Second Sensor Element)

A second sensor element may be a quantum optical sensor that measures an amount of light, may be a soundwave sensor that detects pressure change due to light absorption by a gas, or may simply be a resistive element. It is desirable that the second sensor element can be formed on the same wafer as the first sensor element from a viewpoint of miniaturization. In the present embodiment, the second sensor element is a subsequently described second light-receiving element 40. The gas concentration measurement device 10 may have a configuration that includes the second sensor element or may have a configuration that does not include the second sensor element.

(Light-Emitting Element Drive Section)

The light-emitting element drive section 13 applies a specific current or voltage to the light-emitting element 11 and causes the light-emitting element 11 to emit light with a specific brightness. In the present embodiment, the light-emitting element drive section 13 causes the light-emitting element 11 to emit light through constant-current driving. The light-emitting element drive section 13 may apply current or voltage for driving the light-emitting element 11 as a pulse. A representative example of a pulse signal is a square wave. However, the pulse signal is not limited to a square wave so long as it is a wave form that temporarily undergoes a rapid change at a fixed interval. From a viewpoint of preventing reduction of light emission efficiency due to heat generation, a duty ratio of 50% or less is desirable, a duty ratio of 10% or less is more desirable, a duty ratio of 5% or less is more desirable, and a duty ratio of 1% or less is more desirable. The "duty ratio" referred to here is defined by "emission time/total of emission time and non-emission time".

In another embodiment, the light-emitting element drive section 13 may cause the light-emitting element 11 to emit light through constant-voltage driving.

(Temperature Measurement Section)

The temperature measurement section 14 measures temperature. This temperature is the temperature around where the gas concentration measurement device 10 is used and may be the temperature of the environment in which the gas concentration measurement section 10a is used, the temperature of the gas concentration measurement section 10a itself, or the temperature of the gas concentration measurement device 10 itself. The temperature measurement section 14 may be implemented as a temperature sensor such as a thermistor, a platinum (Pt) resistance thermometer, or a diode, for example. In the present embodiment, the temperature measurement section 14 is a temperature sensor that is included in a subsequently described integrated circuit (IC) 30, but is not limited thereto. In another example, the temperature measurement section 14 may be a resistance value of the light-emitting element 11 itself or may be a resistance value of the first light-receiving element 12 itself. Moreover, the computation section 22 may include the temperature measurement section 14. Furthermore, the subsequently described second light-receiving element 40 may be used as the temperature measurement section 14. In this case, the temperature measurement section 14 may use a resistance value of the second light-receiving element 40 as a temperature output or may use an output signal of the second light-receiving element 40 as a temperature output. In other words, the temperature measurement section 14 may be a temperature acquisition section.

(Signal Acquisition Section)

The signal acquisition section 21 acquires at least an output signal of the first light-receiving element 12 and a drive signal of the light-emitting element 11. The drive signal is a voltage value during constant-current driving of the light-emitting element 11 or is a current value during constant-voltage driving of the light-emitting element 11. In the present embodiment, the drive signal of the light-emitting element 11 is a voltage value and is temperature corrected in accordance with the temperature of the gas concentration measurement device 10 itself. The "output signal" of the first light-receiving element 12 referred to in the present specification is a signal that is output by the first light-receiving element 12 based on the intensity of light detected by the first light-receiving element 12.

The signal acquisition section 21 may have a function of amplifying the drive signal of the light-emitting element 11, the output signal of the first sensor element (first light-receiving element 12), and the like. In the case of constant-current driving of an LED, for example, light is emitted when the drive signal of the light-emitting element 11 is equal to or greater than a threshold voltage. The drive signal of the light-emitting element 11 may be changed in accordance with changing of the amplification ratio by the signal acquisition section 21. A plurality of drive signals for which the amplification ratio is changed may be used in gas concentration computation. For example, one drive signal (first drive signal) may be equal to or greater than the threshold voltage of the light-emitting element 11 and another drive signal (second drive signal) may be equal to or less than the threshold voltage of the light-emitting element 11. The first signal may be a signal for a certain fixed interval in a state equal to or greater than a first voltage value (for example, a first threshold voltage), and the second drive signal may be a signal for a certain fixed interval in a state less than a second voltage value (for example, a second threshold voltage). A first current value may be used instead of the first voltage value. A second current value may be used instead of the second voltage value. Moreover, a case in which the threshold voltage is set as a certain reference potential on an electronic circuit, such as a ground level value, may be used in gas concentration computation. A drive signal for when the light-emitting element 11 emits light and a drive signal for when the light-emitting element 11 does not emit light may be used in gas concentration computation. In a case in which a plurality of drive signals are used in gas concentration computation, a difference between two drive signals may be used. Computation using a plurality of drive signals is desirable from a viewpoint of removing a circuit offset component that changes over time. In a case in which the light-emitting element 11 or the first sensor element has temperature characteristics, it is desirable that correction computation of the drive signal of the light-emitting element 11 is performed using a separately acquired temperature output from a viewpoint of further increasing measurement accuracy. In this case, the temperature output may be used to perform correction computation with respect to a difference between drive signals. In a case in which the light-emitting element 11 or the first sensor element has temperature characteristics, it is desirable that correction computation of the output signal of the first sensor element is performed using a separately acquired temperature output from a viewpoint of further increasing measurement accuracy. It is desirable that a plurality of output signals are acquired and that correction computation is performed using a difference between these output signals from a viewpoint of further increasing measurement accuracy. For example, a first output signal that is the output signal of the first sensor element when the first drive signal is input and a second output signal that is the output signal of the first sensor element when the second drive signal is input may be used in calculation. A correction signal that is corrected from a difference between the first output signal and the second output signal based on temperature information may be computed. The output signal that is output from the first sensor element may be subjected to correction computation using an output signal that is output from a second sensor element (second light-receiving element 40). In a case in which the second sensor element is arranged on the same printed board as the first sensor element, the effect of stress from the printed board on the first sensor element can be corrected. Moreover, in a case in which the second sensor element is molded inside the same resin package as the first sensor element, the effect of stress from the resin package on the first sensor element can be corrected. The stress referred to here can change depending on the moisture absorption state of the printed board or the resin package.

(Mold Resin)

Figure 2:
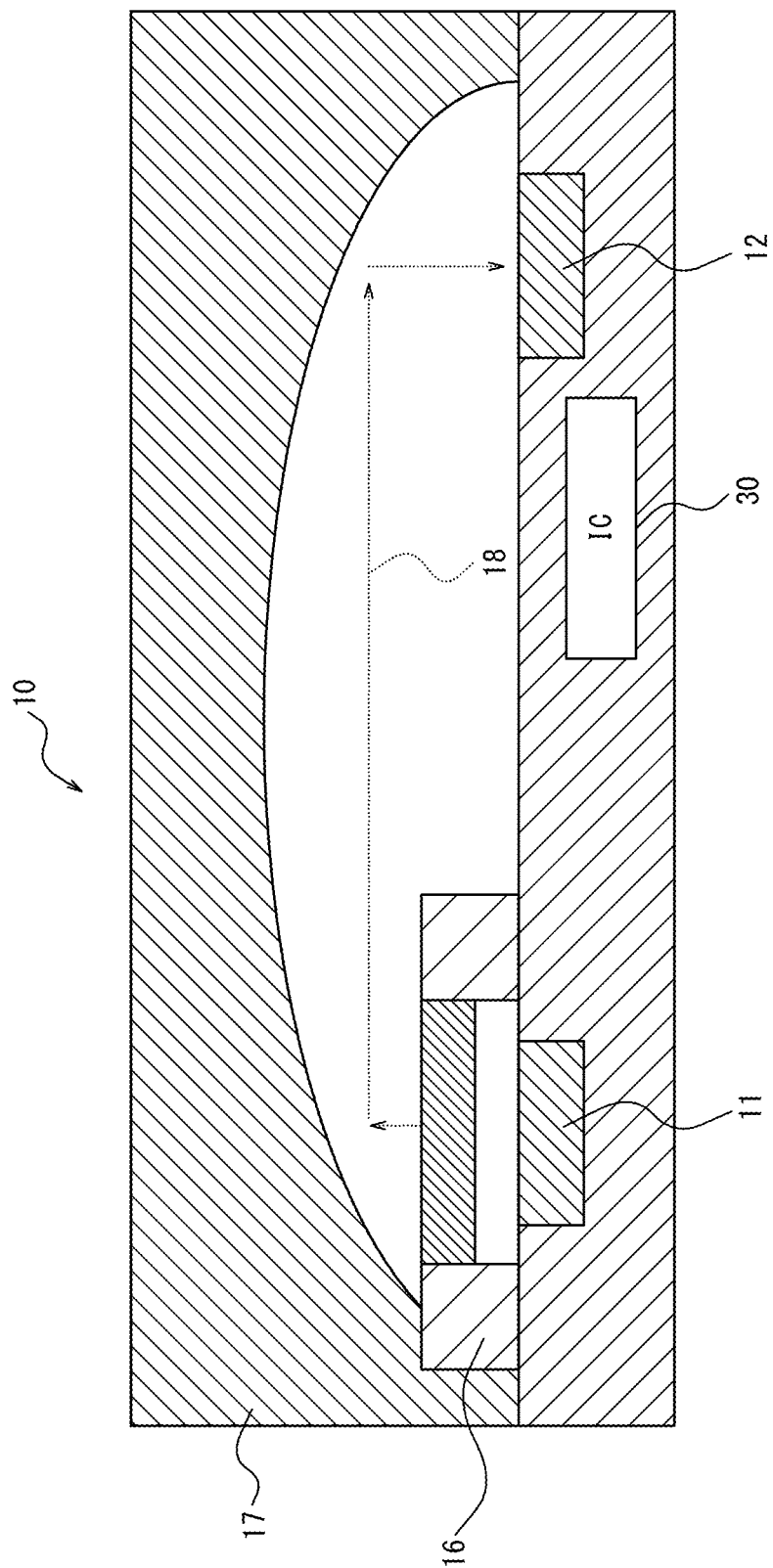
FIG. 2 is a diagram illustrating a configuration example of a gas concentration measurement device according to an embodiment of the present disclosure.

The gas concentration measurement device 10 may have a configuration in which the constituent members described above are packaged together with optical members such as illustrated in FIG. 2. In the gas concentration measurement device 10, at least one of the light-emitting element 11 and the first light-receiving element 12 is sealed by a mold resin. In the example illustrated in FIG. 2, the light-emitting element 11 and the first light-receiving element 12 are sealed together with the IC 30 by the mold resin. The IC 30 can implement functions of the light-emitting element drive section 13, the temperature measurement section 14, and the like. The IC 30 also implements front-end circuitry functions such as amplification circuitry and AD conversion necessary for reading output of the first light-receiving element 12. The IC 30 further implements a function of performing communication with the externally located computation section 22. From a viewpoint of miniaturization, it is preferable that at least the light-emitting element 11 and the first light-receiving element 12 are sealed by the same mold resin, and more preferable that the light-emitting element 11 and the first light-receiving element 12 are sealed together with the IC 30 by the same mold resin. Moreover, it is even more preferable that at least the light-emitting element 11, the first light-receiving element 12, the light-emitting element drive section 13, the signal acquisition section 21, and the temperature measurement section 14 are sealed by the same mold resin.

(Light Guide)

A reflector 17 is also provided in order that light 18 emitted from the light-emitting element 11 is reflected and irradiates the first light-receiving element 12. In other words, in the present embodiment, the gas concentration measurement device 10 includes a reflector 17 functioning as a light guide that guides light 18 from the light-emitting element 11 to the first light-receiving element 12. In the example illustrated in FIG. 2, the reflector 17 is a concave mirror. The reflecting surface of the reflector 17 may be formed of a metal having high reflectance such as aluminum or gold or may be a coating or plating that has a film of any of these metals, for example. Moreover, the light guide may be composed of a plurality of parts. Appropriate optical design of the reflector 17 is necessary in order for the light 18 that has been emitted from the light-emitting element 11 to irradiate the first light-receiving element 12. Although a design that causes some of the light 18 to irradiate the first light-receiving element 12 may be adopted, a design that causes all of the light 18 to irradiate the first light-receiving element 12 is desirable.

(Optical Filter)

In the present embodiment, the gas concentration measurement device 10 includes an optical filter 16 that limits the wavelength of the light 18 as illustrated in FIG. 2. For example, in a case in which the measurement target gas is $CO_2$, the optical filter 16 may be a bandpass filter that transmits infrared light in a wavelength band in which significant absorption of infrared light by $CO_2$ occurs (typically around 4.3 μm). In a case in which the measurement target gas is methane, the optical filter 16 may be a bandpass filter that transmits infrared light in a wavelength band in which significant absorption of infrared light by methane occurs (typically around 3.4 μm). In a case in which the measurement target gas is alcohol, the optical filter 16 may be a bandpass filter that transmits infrared light in a wavelength band in which significant absorption of infrared light by alcohol occurs (typically around 3.4 μm to 3.7 μm or around 9.5 μm). This optical filter may be provided at any location along an optical path that the light 18 emitted from the light-emitting element 11 travels until it is received by the first light-receiving element 12. Moreover, the optical filter 16 may be formed by coating on the light-emitting element 11, the first light-receiving element 12, and/or the light guide.

(Diode Structure)

In the present embodiment, the light-emitting element 11 is an infrared LED. Moreover, in the present embodiment, the first light-receiving element 12 is a quantum infrared sensor. At least one of the light-emitting element 11 and the first light-receiving element 12 may contain at least one of indium and gallium and at least one of arsenic and antimony as materials and have a diode structure that at least includes two types of layers of a p-type semiconductor and an n-type semiconductor.

(Control Section)

The control section 24 controls overall operation of the gas concentration measurement device 10 and also has a communication function of outputting signals acquired by the signal acquisition section 21 to the computation section 22, for example. Functions of the control section 24 may be implemented by software or may be implemented by hardware. The computation section 22 may be implemented by a microcontroller unit, for example.

(Data Storage Section)

The data storage section 23 stores data used by the control section 24 to control the gas concentration measurement device 10. The data storage section 23 may be composed of at least one memory. The memory may be semiconductor memory, magnetic memory, optical memory, or the like, for example, but can be any memory without limitation to these examples.

<Parameter Set Storage Section>

The parameter set storage section 15 stores a correction parameter set for correction of the output signal of the first light-receiving element 12. The parameter set storage section 15 may be composed of at least one memory. The memory may be semiconductor memory, magnetic memory, optical memory, or the like, for example, but can be any memory without limitation to these examples. The correction parameter set may be composed of a combination of correction parameters that are based on a commonly known temperature correction technique. The parameter set storage section 15 may, for example, store polynomial approximation coefficients in advance. The correction parameter set is used by the computation section 22 to correct temperature information, for example. No limitations are placed on the arrangement location of the parameter set storage section 15 so long as it can be accessed by the computation section 22, etc. The parameter set storage section 15 may be included in the subsequently described IC 30, may be included in the computation section 22, or may be included in another element in the gas concentration measurement system 1.

<Computation Section>

The computation section 22 computes a gas concentration based on signals acquired by the signal acquisition section 21. The computation section 22 can also be referred to as a gas concentration computation section. In the present embodiment, the light-emitting element 11 emits light with a specific brightness. The computation section 22 computes the gas concentration from the output signal of the first light-receiving element 12 based on the received amount of light of a wavelength that is absorbed by the measurement target gas, for example. For example, the computation section 22 may compute the gas concentration through comparison with the received amount of light in a situation in which the measurement target gas is not present or may compute the gas concentration through comparison with the received amount of light in a situation in which a fixed amount of the measurement target gas is present.

Functions of the computation section 22 may be implemented by software or may be implemented by hardware. The computation section 22 may be implemented by a microcontroller unit, for example. The computation section 22 may be implemented as an individual device in the form of a computation device. Alternatively, the computation section 22 may be implemented by the IC 30 of the gas concentration measurement device 10. In this case, the gas concentration measurement device 10 is a device having the computation section 22 incorporated therein and may individually constitute the gas concentration measurement system 1.

Figure 7:
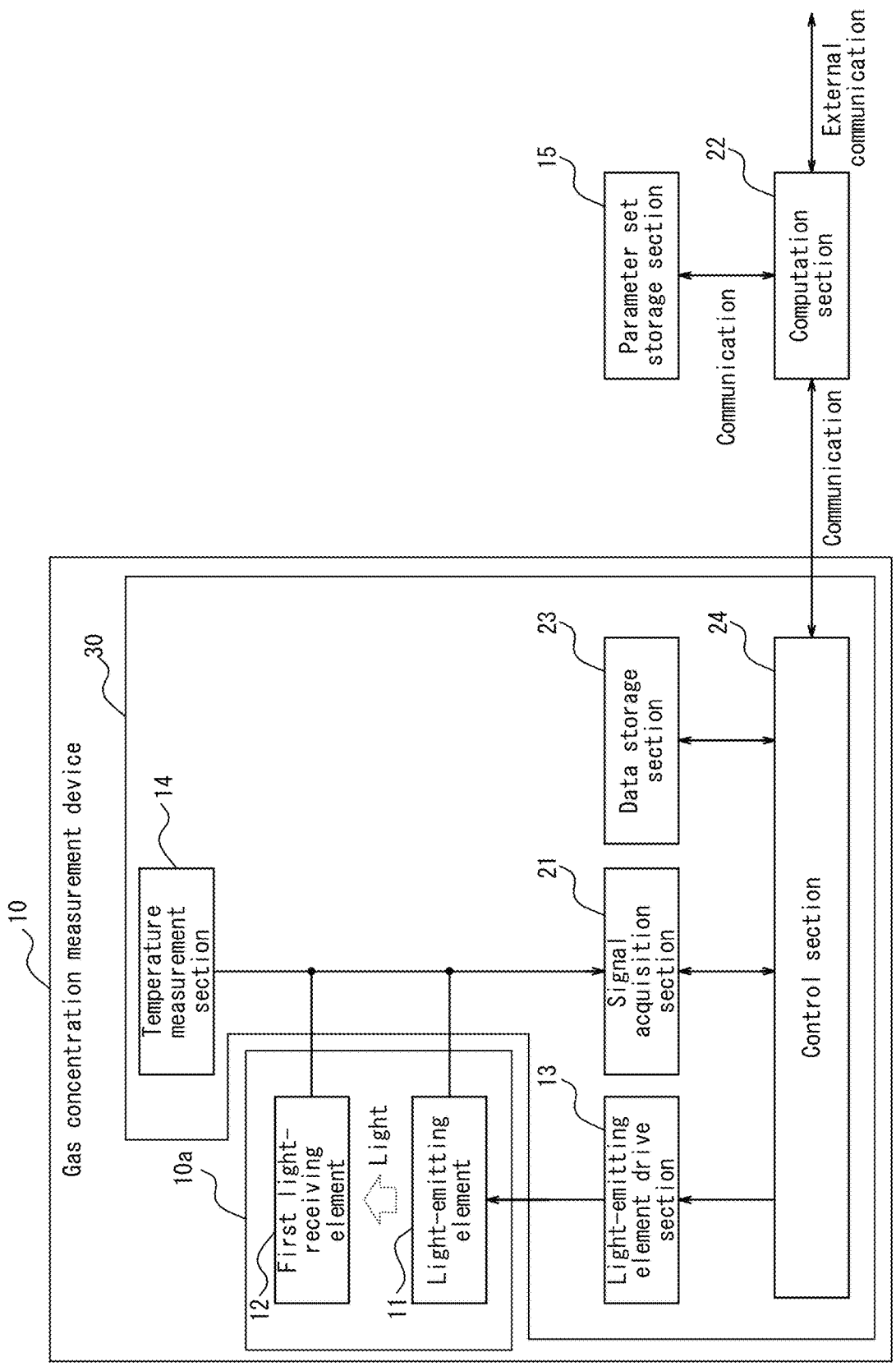
FIG. 7 is a diagram illustrating a specific configuration example of the gas concentration measurement system illustrated in FIG. 1.
Figure 8:
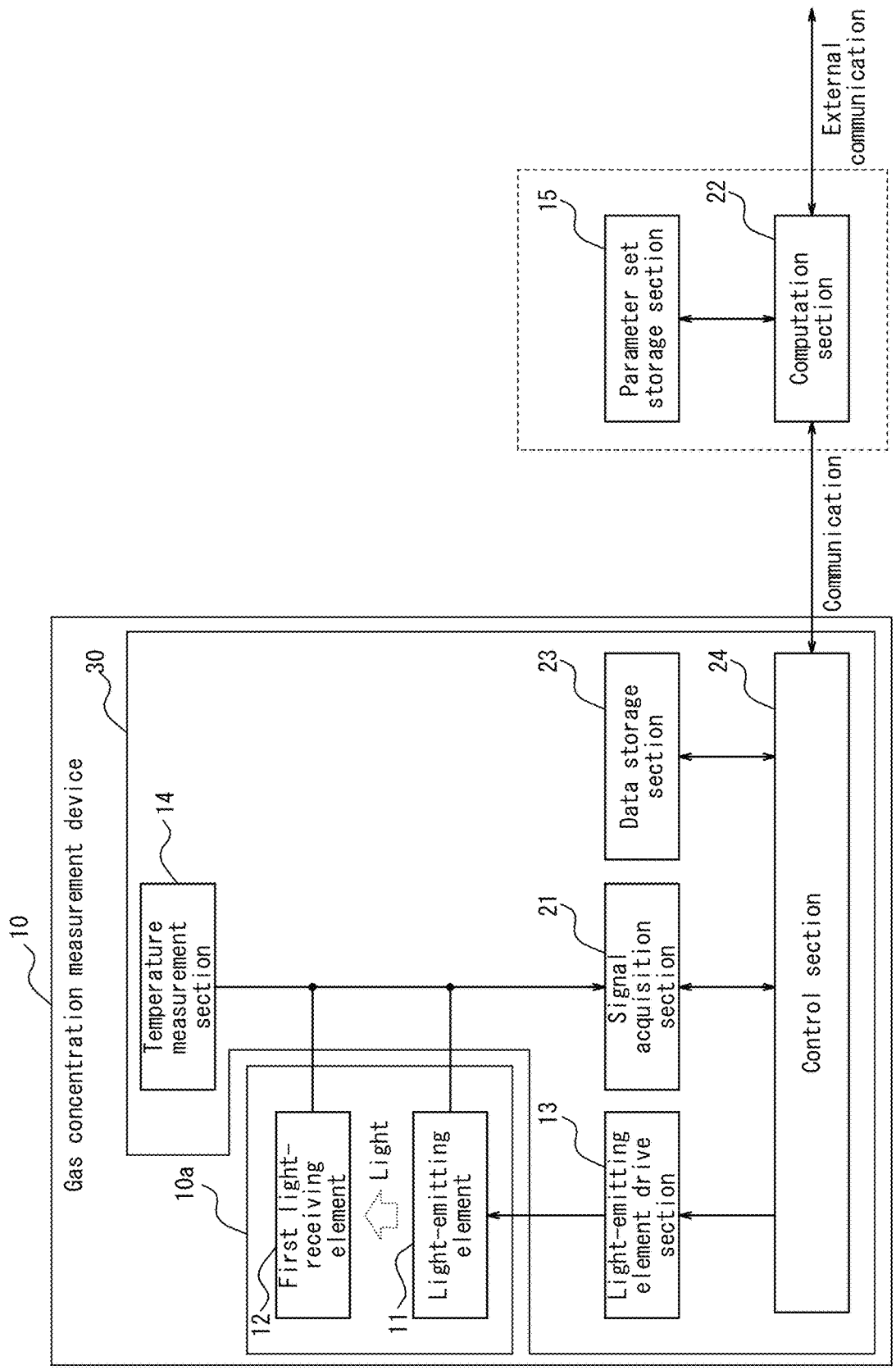
FIG. 8 is a diagram illustrating a specific configuration example of the gas concentration measurement system illustrated in FIG. 1.
Figure 9:
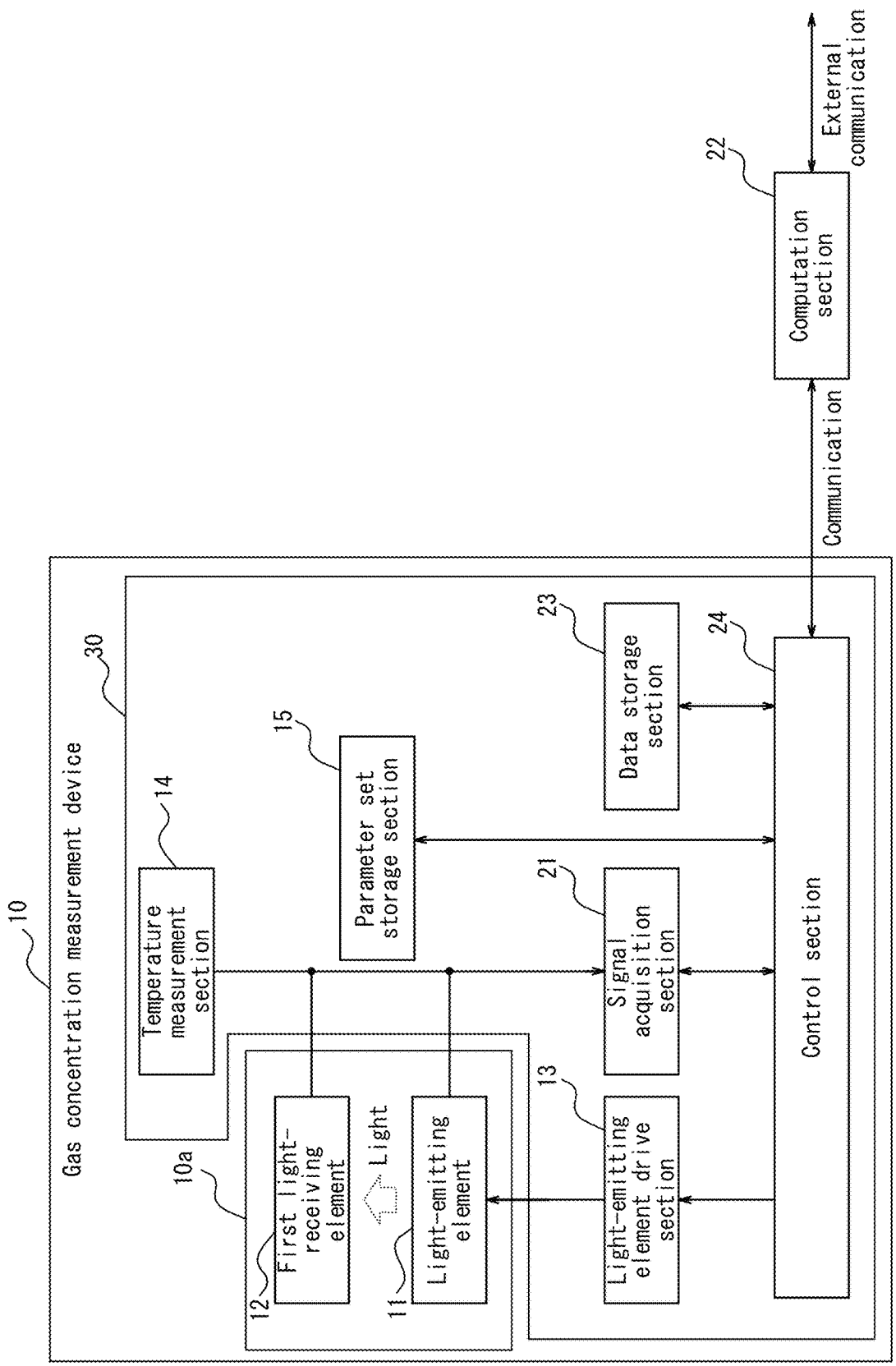
FIG. 9 is a diagram illustrating a specific configuration example of the gas concentration measurement system illustrated in FIG. 1.
Figure 10:
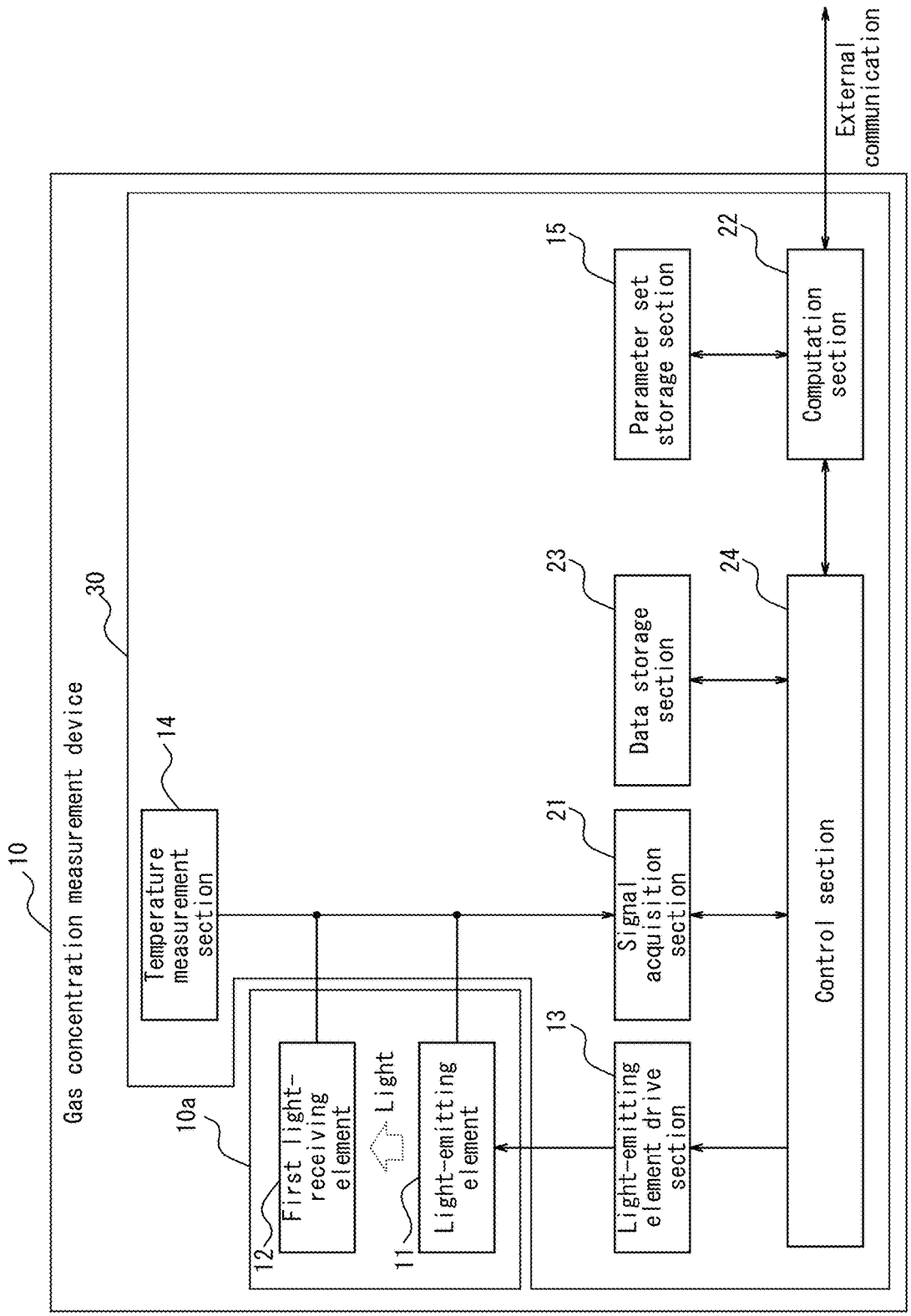
FIG. 10 is a diagram illustrating a specific configuration example of the gas concentration measurement system illustrated in FIG. 1.

Note that in the gas concentration measurement system 1, the scope (configuration) of the gas concentration measurement device 10 indicated by the dashed line in FIG. 1 is merely one example. In a case in which the gas concentration measurement device 10 includes the IC 30 as illustrated in FIG. 2, various configurations can be adopted without any limitations on which functional sections are implemented by the IC 30. FIGS. 7 to 10 are diagrams that each illustrate a specific configuration example of the gas concentration measurement system 1 illustrated in FIG. 1. For example, functions of the light-emitting element drive section 13, the temperature measurement section 14, the signal acquisition section 21, the data storage section 23, and the control section 24 may be implemented by the IC 30 as illustrated in FIG. 7. In this case, the control section 24 may transmit and receive data through communication with the computation section 22, which functions individually as a computation device. Moreover, the computation section 22 may have a function of communication with an external device and may perform communication with the parameter set storage section 15, for example, which is an external device relative to the computation section 22. The parameter set storage section 15 and the computation section 22 can be configured as an integrated device, for example, as illustrated in FIG. 8. Moreover, a configuration such as illustrated in FIG. 9 in which the parameter set storage section 15 is included in the IC 30 of the gas concentration measurement device 10 and in which the computation section 22 acquires the correction parameter set through communication via the control section 24 can also be adopted. Furthermore, a configuration such as illustrated in FIG. 10 in which the computation section 22 is included in the IC 30 of the gas concentration measurement device 10 and in which the gas concentration measurement device 10 individually implements the gas concentration measurement system 1 can also be adopted. In another configuration example, the temperature measurement section 14 may be provided externally to the IC 30. In this case, the temperature measurement section 14 may be the first light-receiving element 12, and a resistance value or output signal of the first light-receiving element 12 may be used as a temperature output. Alternatively, the temperature measurement section 14 may be the light-emitting element 11, and a resistance value of the light-emitting element 11 may be used as a temperature output. Furthermore, in a case in which the computation section 22 is configured by a microcontroller unit, the temperature measurement section 14 may be included in the microcontroller unit together with the computation section 22. In FIGS. 7 to 10, the computation section 22 is illustrated as performing external communication. However, the control section 24 may perform communication with the computation section 22 and also perform communication with an external device other than the computation section 22.

In the present embodiment, the gas concentration measurement device 10 has a configuration in which the light-emitting element 11 and the first light-receiving element 12 are sealed by a mold resin. Consequently, variation of the amount of light emission by the light-emitting element 11 and the output signal of the first light-receiving element 12 may arise under the influence of swelling stress that is caused by moisture absorption or drying of the resin depending on the humidity. Variation of the amount of light emission by the light-emitting element 11 and the output signal of the first light-receiving element 12 can also arise under the influence of stress (hereinafter, referred to as physical stress) that is caused by external force or the like other than swelling stress. Particularly in the case of a miniaturized gas concentration measurement device 10, there is a short optical path length, and a slight effect due to stress can cause significant reduction of detection accuracy. Therefore, in order to perform high-accuracy gas concentration measurement, it is necessary to correct variation of the output signal of the first light-receiving element 12 that arises under the influence of such stress and then compute the gas concentration.

The computation section 22 determines a first signal, a second signal, and a third signal by computation and then computes the gas concentration based on the third signal as described below. The first signal is computed, based on temperature, from a forward voltage ($V_f$) of the LED obtained during constant-current driving. The second signal is computed based on the output signal of the first light-receiving element 12. The third signal is computed from the second signal based on the first signal and is a value that can be converted to a gas concentration.

In the present embodiment, current is applied as a pulse, a difference between a voltage Vf1 when light is emitted and a voltage Vf2 when light is not emitted is taken to be $dV_f$, and correction computation is performed based on temperature information. In other words, when the temperature is taken to be T, the first signal (signal1) is indicated by the following formula (1).

$$\text{signal1} = (Vf1 - Vf2) \times f_1(T) = dV_f \times f_1(T) \qquad (1)$$

In formula (1), $dV_f$ is the difference between drive signals (forward voltage generated in the light-emitting diode during constant-current driving) during pulse driving. Moreover, $f_1(T)$ is a temperature correction coefficient. Offset variation can arise over the long-term for an amplifier or the like for signal amplification that is included in the signal acquisition section 21, which is at a later stage than the light-emitting element drive section, the light-emitting element, the first light-receiving element, and so forth. In the present embodiment, it is preferable to take the difference between the voltage Vf1 when light is emitted and the voltage Vf2 when light is not emitted from of viewpoint of improving long-term stability. The difference $dV_f$ between Vf1 and Vf2 is used in computation in the present embodiment, but it should be possible to remove a long-term offset variation component through computation based on Vf1 and Vf2.

The second signal may be the output signal of the first light-receiving element 12. In this case, the second signal (signal2) is indicated by the following formula (2).

$$\text{signal2} = \text{main} \qquad (2)$$

In formula (2), "main" is the output signal of the first light-receiving element 12.

Figure 3:
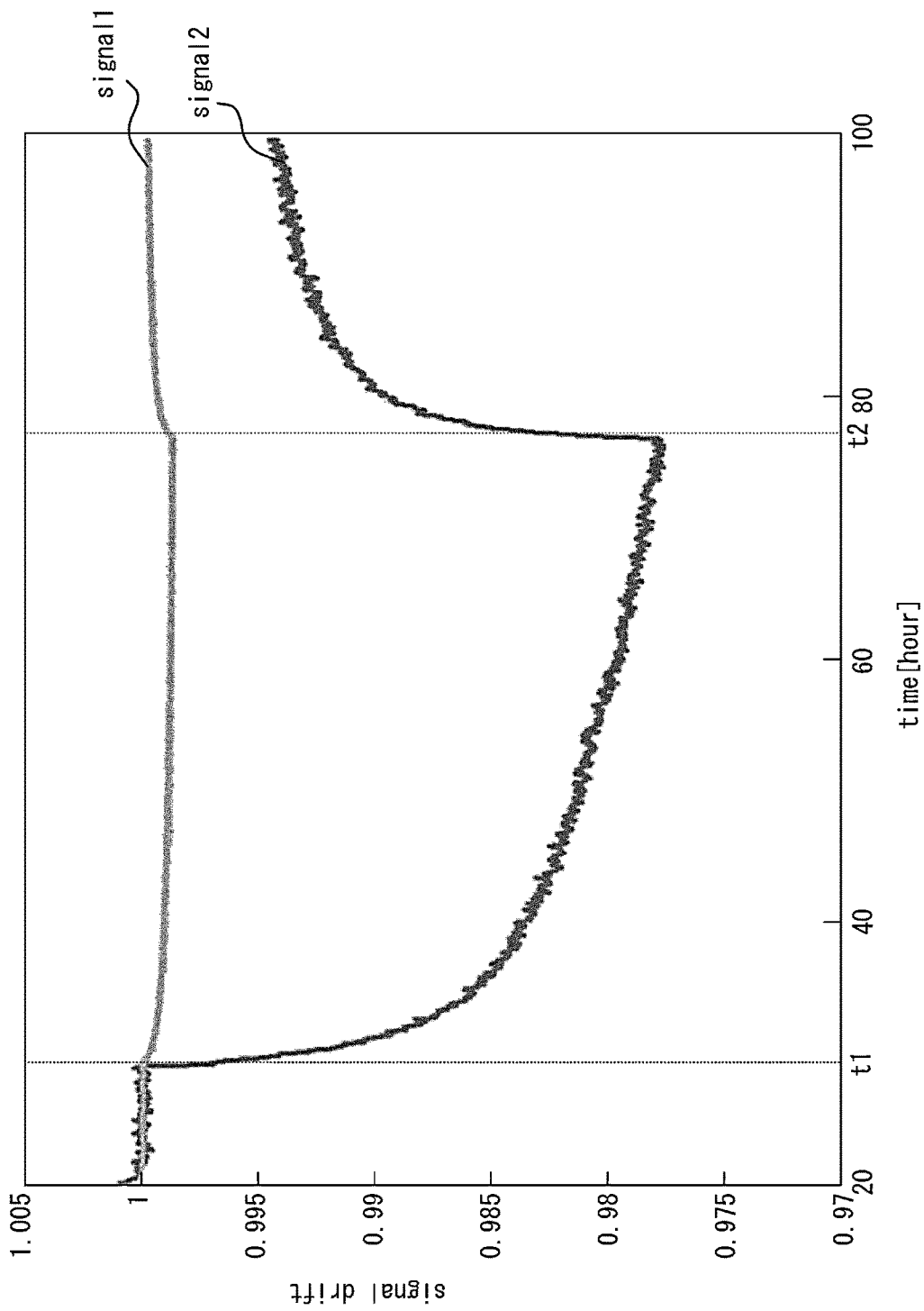
FIG. 3 is a diagram for describing a relationship between a first signal and a second signal.
Figure 4:
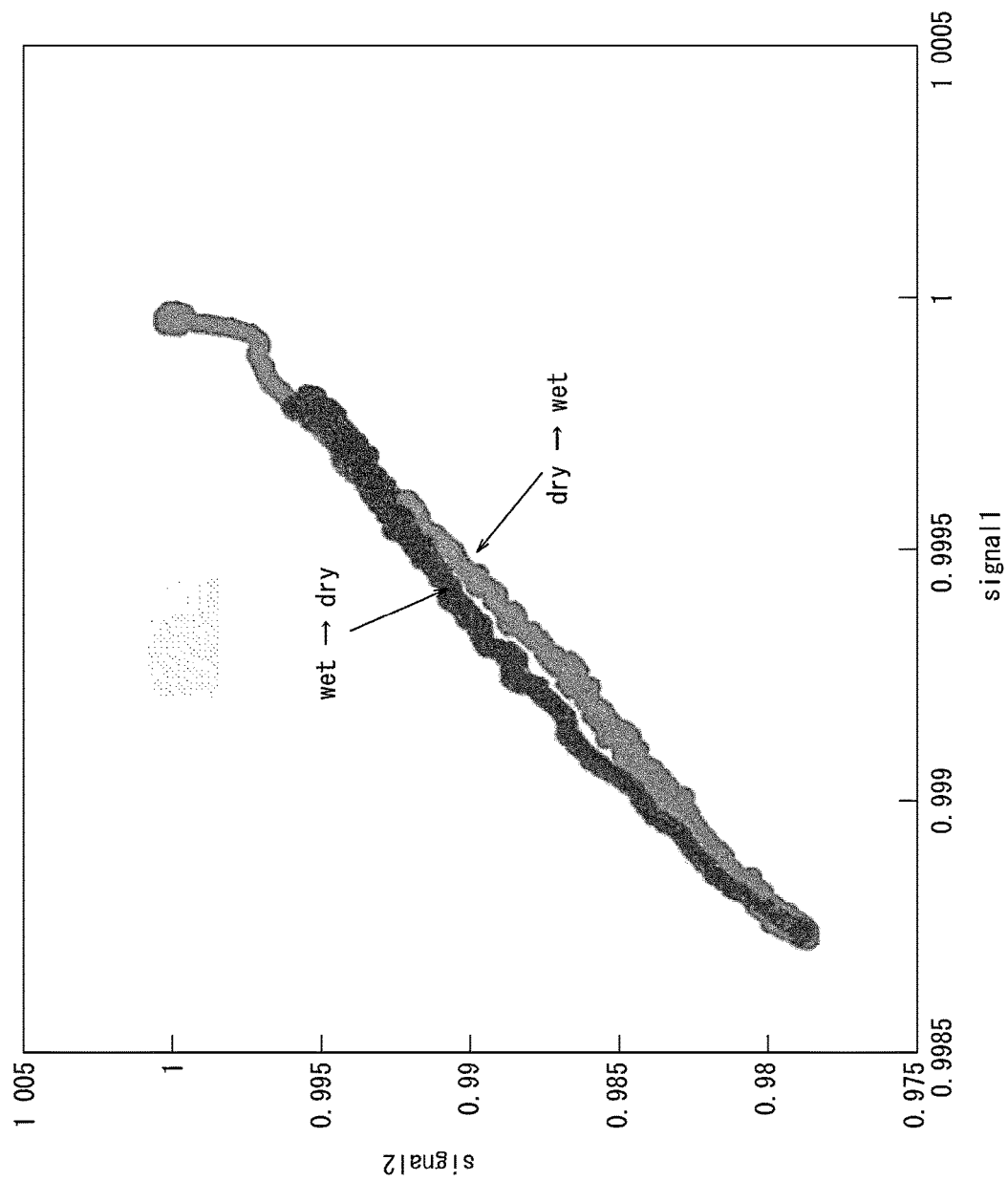
FIG. 4 is another diagram for describing a relationship between the first signal and the second signal.

FIGS. 3 and 4 were obtained by intentionally causing swelling stress to arise in the gas concentration measurement device 10 and investigating changes of the first signal and the second signal and a relationship therebetween. The horizontal axis in FIG. 3 is a time axis. Moreover, the vertical axis (signal drift) in FIG. 3 indicates variation of values of the first signal and the second signal. The gas concentration measurement device 10 was exposed to high-humidity air from time t1 to time t2 indicated in FIG. 3 so as to cause moisture absorption by resin. At the time t2, the gas concentration measurement device 10 was exposed to dry air in the same manner as prior to the time t1. The first signal and the second signal both decrease under the influence of swelling stress from the time t1 onwards. Moreover, the first signal and the second signal both change back toward 1 from the time t2 onwards.

FIG. 4 is a diagram in which the first signal and the second signal at the same time in FIG. 3 are respectively plotted on the horizontal axis and the vertical axis. The first signal and the second signal up until the time t2 are indicated by "dry→wet". Moreover, the first signal and the second signal from the time t2 onwards are indicated by "wet→dry". The first signal and the second signal are correlated as illustrated in FIG. 4. Variation of the first signal can be converted to variation of the second signal by the following formula (3) using linear expression coefficients a and b. In the present embodiment, the first signal, the second signal, and the third signal prior to being affected by stress are normalized, and the first signal, the second signal, and the third signal are each "1", which means that a+b=1 is valid. In other words, a+b=1 is valid such as to satisfy signal1(T)=1, signal2=1, and signal3=1 in the subsequently described formula (4).

Although a+b=1 is valid in the present embodiment, it is not necessarily the case that a+b=1 depending on the calculation method. A non-linear case may arise depending on the state of application of stress, etc. In a case in which the first signal and the second signal are non-linear, a plurality of intermediate states may be measured and linear interpolation may be performed between these measurement points, or a polynomial approximation or the like may be made. In any of these cases, at least one independent term (independent correction coefficient) and at least one dependent term (dependent correction coefficient) may be included. The dependent correction coefficient is dependent on the independent correction coefficient.

$$g(signal1(T))=a\times(signal1(T))+b$$

$$signal1(T)=dV_f \times f_1(T) \quad (3)$$

The computation section 22 can use the above-described relationship of the first signal and the second signal to correct the effect of stress on the output signal of the first light-receiving element 12, for example. When stress has an effect, the first signal varies as illustrated for the time t1 onwards in FIG. 3. Variation of the first signal can be converted to variation of the second signal using formula (3). The third signal, which is the second signal after correction of the effect of stress, is obtained through multiplication by a reciprocal of the variation of the second signal (g(signal1(T))) determined by this conversion. The third signal (signal3) is indicated by the following formula (4). The third signal is calculated using at least one independent correction coefficient and a dependent correction coefficient. The computation method of multiplying by the reciprocal of the converted variation of the second signal that is adopted when determining the third signal is merely one example and is not a limitation. Moreover, correction of the effect of stress may be by computation performed using polynomial approximation, a plurality of linear approximations, or a curve.

$$signal3 = \frac{signal2}{g(signal1(T))} = \frac{signal2}{a\times(signal1(T))+b} \quad (4)$$

The computation section 22 computes the gas concentration based on the third signal that is corrected from the second signal based on the first signal. For example, the computation section 22 may acquire a calibration curve linking the third signal and gas concentration in advance and may compute the gas concentration from a value of the third signal. As a result of the computation section 22 performing computation processing such as set forth above, the gas concentration measurement system 1 is capable of high-accuracy gas concentration measurement in which the effect of stress has been corrected. In the example illustrated in FIG. 3 and FIG. 4, stress is induced in the gas concentration measurement device 10 through humidity, but humidity information is not used in the computation processing by the computation section 22. In other words, the gas concentration measurement system 1 can correct the effect of stress in a manner that is also inclusive of physical stress, for example, without limitation to swelling stress.

The second signal may be computed from the output signal of the first light-receiving element 12 based on the temperature T. In this case, the following formula (5) is used instead of the previously described formula (2).

$$signal2(T)=main\times f_2(T) \quad (5)$$

In formula (5), $f_2(T)$ is a function for correcting the output signal based on the temperature. Performing correction of the output signal of the first light-receiving element 12 based on the temperature enables even higher accuracy gas concentration measurement.

Figure 11:
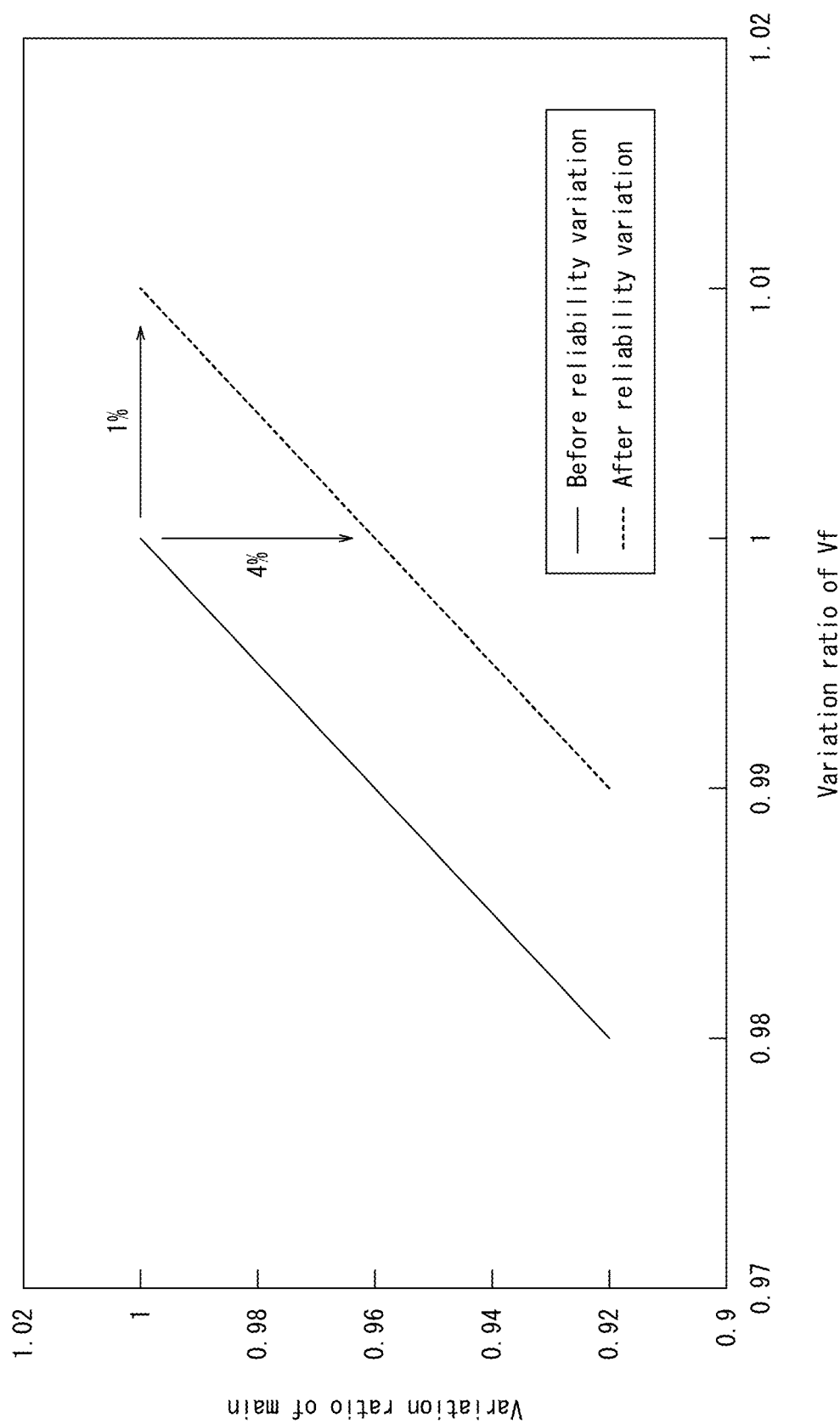
FIG. 11 is an example of correction curve variation in a case in which difference computation (Vf1−Vf2) is not performed.
Figure 12:
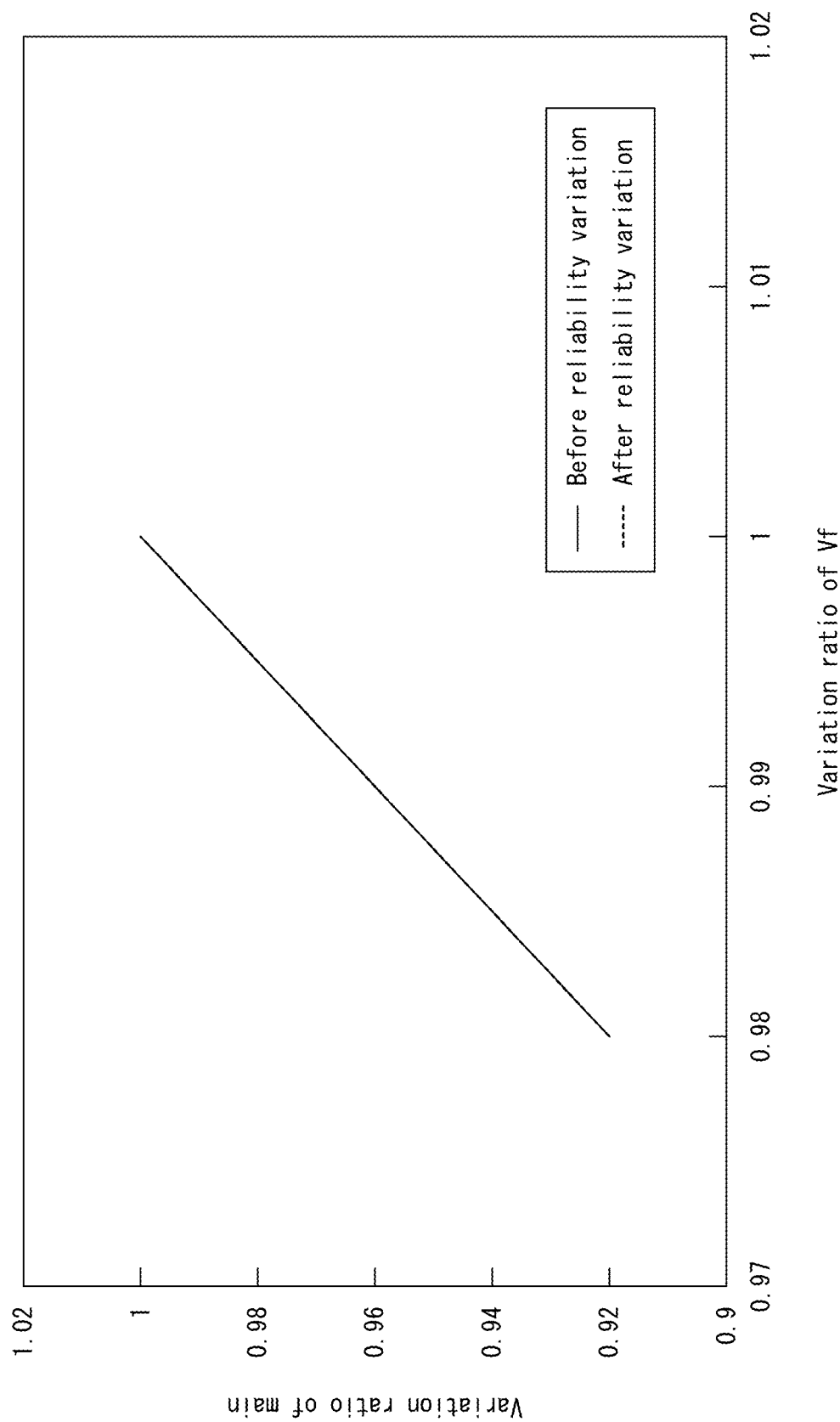
FIG. 12 is an example of correction curve variation in a case in which difference computation (Vf1−Vf2) is performed.

Moreover, the computation section 22 may compute a moving average of at least one of the drive signal and the output signal of the first light-receiving element 12 and may use a value of the moving average to compute at least one of the first signal and the second signal. The use of a moving average reduces the effect of noise and enables even higher accuracy gas concentration measurement. In a case in which difference computation (Vf1−Vf2) is not performed, there is a possibility that gas concentration computation cannot be performed correctly due to variation of a coefficient for correction computation or the like in a situation in which reliability variation of the signal acquisition section arises. FIG. 11 is an example of correction curve variation in a situation in which there is 1% variation of offset of a drive signal. In this example, the variation ratio of "main" is 4%. Such variation becomes fatal as the optical path length constructed by the light guide becomes shorter. In a case in which the difference calculation (Vf1−Vf2) is performed, even when reliability variation of the signal acquisition section arises, offset can be removed by taking the difference, and thus correction curve variation due to reliability variation does not arise as illustrated in FIG. 12. Consequently, high accuracy can be maintained in gas concentration computation.

<Gas Concentration Measurement Method>

Figure 5:
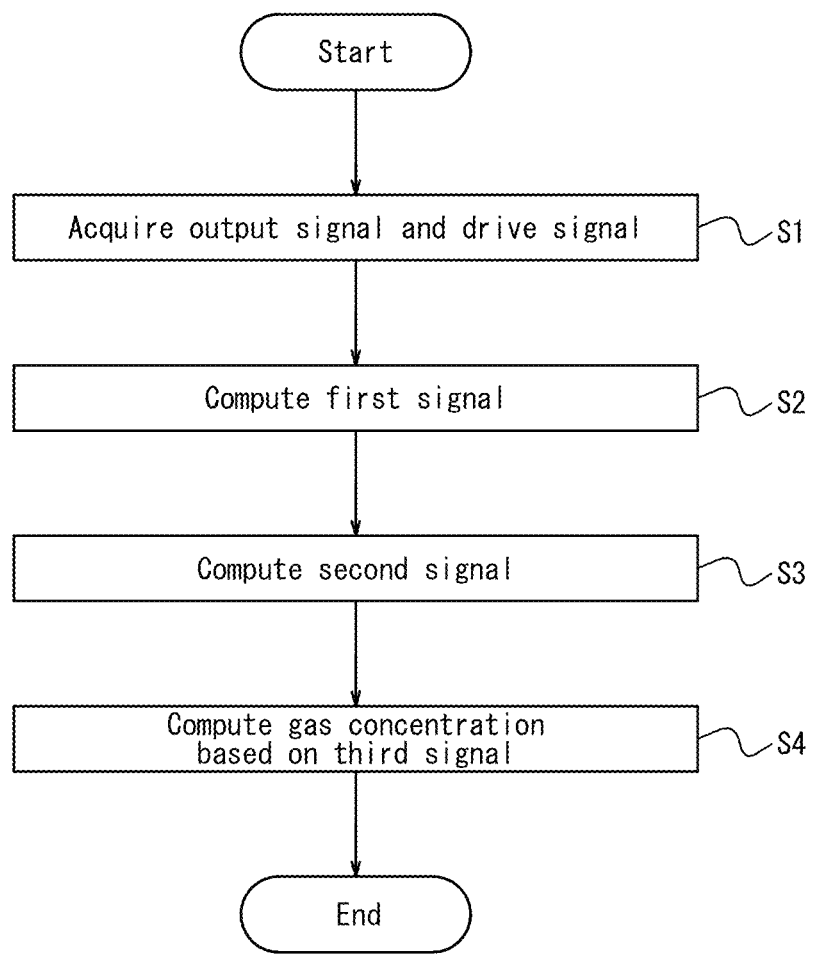
FIG. 5 is a flowchart illustrating an example of a gas concentration measurement method according to an embodiment of the present disclosure.

In the gas concentration measurement system 1 according to the present embodiment, the computation section 22 performs a gas concentration measurement method described below to compute the gas concentration. FIG. 5 is a flowchart illustrating an example of the gas concentration measurement method.

The computation section 22 acquires the output signal of the first light-receiving element 12 and the drive signal. The computation section 22 may also acquire the temperature (Step S1).

The computation section 22 computes the first signal as previously described (Step S2).

The computation section 22 computes the second signal as previously described (Step S3).

The computation section 22 computes the third signal and computes the gas concentration based on the third signal as previously described (Step S4).

In this manner, the gas concentration measurement system 1, the gas concentration computation section, and the gas concentration measurement method according to the present embodiment enable high-accuracy gas concentration measurement through the configuration or steps set forth above.

Although an embodiment of the present disclosure has been described based on the various drawings and examples, it should be noted that a person of ordinary skill in the art could easily make various modifications and revisions based on the present disclosure. Accordingly, such modifications and revisions should also be considered to be included within the scope of the present disclosure. For example, functions and the like included in various constituent parts, various steps, etc., can be rearranged so long as they are logically consistent. Moreover, a plurality of constituent parts, steps, etc. can be combined as one or can be split up. The embodiment according to the present disclosure can also be realized as a program that is run by a processor included in a device or as a storage medium in which a program is recorded. It should be appreciated that these are also included within the scope of the present disclosure.

Figure 6:
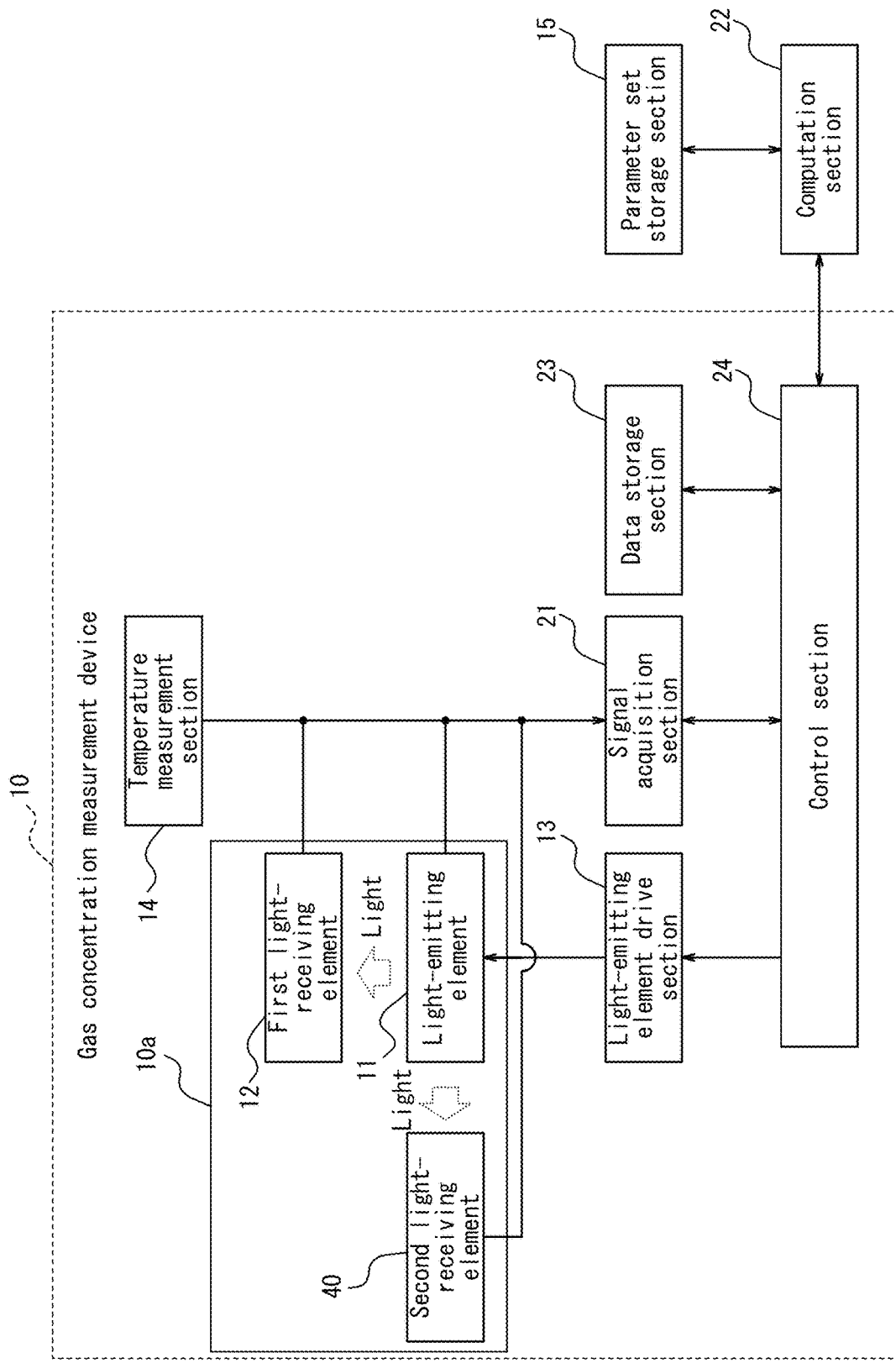
FIG. 6 is a diagram illustrating another configuration example of a gas concentration measurement system.

For example, the gas concentration measurement device 10 may include a second light-receiving element 40 that does not have sensitivity to the measurement target gas as illustrated in FIG. 6. The computation section 22 can determine the received amount of light in a situation in which there is no absorption by the measurement target gas from an output signal of the second light-receiving element 40. The "output signal" of the second light-receiving element 40 is a signal that is output by the second light-receiving element 40 based on the intensity of light detected by the second light-receiving element 40. Through comparison of the output signal of the first light-receiving element 12 and the output signal of the second light-receiving element 40, the computation section 22 can more accurately compute the received amount of light for which there has been absorption by the measurement target gas. In the configuration illustrated in FIG. 6, the second signal may be computed based on the output signal of the first light-receiving element 12 and the output signal of the second light-receiving element 40. By using the output signal of the second light-receiving element 40 in computation of the second signal, more accurate computation is also possible with regard to correction of the effect of stress. The configuration of the second light-receiving element 40 may be the same as the configuration of the first light-receiving element 12.

The invention claimed is:

1. A gas concentration measurement system comprising:
    a gas concentration measurement section including a light-emitting element and a first sensor element;
    a light-emitting element drive section that drives the light-emitting element;
    a signal acquisition section that acquires at least an output signal of the first sensor element, a first drive signal that is a first voltage value or a first current value of the light-emitting element, and a second drive signal that is a second voltage value or a second current value of the light-emitting element; and
    a computation section that computes a gas concentration based on signals acquired by the signal acquisition section, wherein
    the computation section, based on the first drive signal and the second drive signal, corrects the output signal of the first sensor element and computes the gas concentration.

2. The gas concentration measurement system according to claim 1, wherein the first sensor element is a light-receiving element that detects light.

3. The gas concentration measurement system according to claim 1, wherein
    the first drive signal is a signal for a certain fixed interval in a state of equal to or greater than a first threshold voltage, and
    the second drive signal is a signal for a certain fixed interval in a state of equal to or less than a second threshold voltage.

4. The gas concentration measurement system according to claim 3, wherein the second threshold voltage is a circuit ground level value.

5. The gas concentration measurement system according to claim 1, wherein the computation section computes a difference between the first drive signal and the second drive signal and, based on the difference, corrects the output signal of the first sensor element and computes the gas concentration.

6. The gas concentration measurement system according to claim 1, wherein
    the first drive signal is a signal for when the light-emitting element emits light, and
    the second drive signal is a signal for when the light-emitting element does not emit light.

7. The gas concentration measurement system according to claim 1, further comprising a temperature acquisition section that acquires temperature, wherein the gas concentration measurement system, based on the first drive signal, the second drive signal, and temperature information acquired by the temperature acquisition section, corrects the output signal of the first sensor element and computes the gas concentration.

8. The gas concentration measurement system according to claim 7, wherein the gas concentration measurement system uses a first signal corrected from a difference between the first drive signal and the second drive signal based on the temperature information to correct the output signal of the first sensor element and compute the gas concentration.

9. The gas concentration measurement system according to claim 8, wherein the gas concentration measurement system computes a second signal corrected from the output signal of the first sensor element based on the temperature information, and computes the gas concentration based on the first signal and the second signal.

10. The gas concentration measurement system according to claim 8, wherein the gas concentration measurement system acquires a first output signal that is the output signal of the first sensor element when the first drive signal is being input and a second output signal that is the output signal of the first sensor element when the second drive signal is being input, computes a correction signal corrected from a difference between the first output signal and the second output signal based on the temperature information, and computes the gas concentration based on the first signal and the correction signal.

11. The gas concentration measurement system according to claim 10, wherein the correction signal is calculated using at least one independent correction coefficient and a dependent correction coefficient that is dependent on the independent correction coefficient.

12. The gas concentration measurement system according to claim 1, wherein
    the gas concentration measurement section includes a second sensor element,
    the signal acquisition section acquires an output signal from the first sensor element, and
    the computation section, based on the first drive signal, the second drive signal, and an output signal of the second sensor element, corrects the output signal of the first sensor element and computes the gas concentration.

13. The gas concentration measurement system according to claim 1, wherein the light-emitting element drive section drives the light-emitting element through a pulse signal.

14. The gas concentration measurement system according to claim 1, wherein the light-emitting element is an LED.

15. The gas concentration measurement system according to claim 1, wherein the first sensor element is a light-receiving element, and
the gas concentration measurement system further comprises a light guide that guides light from the light-emitting element to the first sensor element.

16. The gas concentration measurement system according to claim 15, further comprising an optical filter that is provided in an optical path along which light emitted from the light-emitting element travels until it is received by the first sensor element and that limits wavelength of the light.

* * * * *